United States Patent [19]
Pastor et al.

[11] Patent Number: 5,624,983
[45] Date of Patent: Apr. 29, 1997

[54] AMORPHOUS MODIFICATION OF 1,1',1"-NITRILO(TRIETHYL-TRIS-[2,2'-METHYLENE-BIS(4,6-DI-TERT-BUTYLPHENYL)] PHOSPHITE)

[75] Inventors: Stephen D. Pastor, Danbury, Conn.; Sai P. Shum, Pleasantville, N.Y.

[73] Assignee: Ciba-Geigy Corporation, Tarrytown, N.Y.

[21] Appl. No.: 556,775

[22] Filed: Nov. 2, 1995

[51] Int. Cl.$^6$ .......................... C08K 5/527; C07F 9/6574
[52] U.S. Cl. .......................... 524/119; 252/182.29; 554/3; 508/422
[58] Field of Search .......................... 252/46.6, 182.29; 554/3; 524/119

[56] References Cited

U.S. PATENT DOCUMENTS

| | | | |
|---|---|---|---|
| 4,318,845 | 3/1982 | Spivack et al. | 524/91 |
| 4,374,219 | 2/1983 | Spivack et al. | 524/91 |
| 5,326,802 | 7/1994 | Pastor et al. | 524/119 |
| 5,331,031 | 7/1994 | Pastor et al. | 524/119 |
| 5,334,739 | 8/1994 | Pastor et al. | 524/119 |
| 5,334,860 | 8/1994 | Pastor et al. | 524/119 |
| 5,373,040 | 12/1994 | Pastor et al. | 524/119 |
| 5,405,893 | 4/1995 | Pastor et al. | 524/119 |
| 5,486,641 | 1/1996 | Shum et al. | 524/119 |
| 5,489,635 | 2/1996 | Shum et al. | 524/119 |
| 5,489,636 | 2/1996 | Shum et al. | 524/119 |
| 5,512,621 | 4/1996 | Pastor et al. | 524/119 |

*Primary Examiner*—Veronica P. Hoke
*Attorney, Agent, or Firm*—Luther A. R. Hall

[57] ABSTRACT

The new amorphous modification of 1,1',1"-nitrilo{triethyl-tris-[2,2'-methylene-bis(4,6-di-tert-butylphenyl)]phosphite} is obtained by cooling rapidly said compound from the melt to ambient temperature. This amorphous form is an effective process stabilizer for polyolefins, particularly polypropylene.

14 Claims, No Drawings

AMORPHOUS MODIFICATION OF 1,1',1"-NITRILO(TRIETHYL-TRIS-[2,2'-METHYLENE-BIS(4,6-DI-TERT-BUTYLPHENYL)] PHOSPHITE)

This invention pertains to a novel amorphous modification of 1,1',1"-nitrilo-{triethyl-tris-[2,2'-methylene-bis(4,6-di-tert-butylphenyl)]phosphite}, to a process for preparing said modification, and to compositions stabilized therewith.

BACKGROUND OF THE INVENTION 1,1',1"-Nitrilo{triethyl-tris-[2,2'-methylene-bis(4,6-di-tert-butylphenyl)]phosphite} is a compound having the formula I

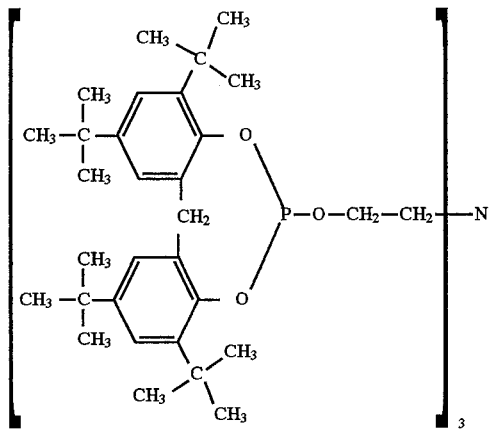

This compound of formula I is useful as a processing stabilizer for organic polymers as taught in U.S. Pat. Nos. 4,318,845 and 4,374,219. The compound of formula I is disclosed as being a white powder melting at 175°–181° C. The relatively high melting point of the "white powder" form of the compound of formula I as disclosed in the above mentioned patents is a problem when stabilizing organic polymers processed at relatively low temperatures such as blow molding of HDPE and processing of natural rubber. As a result, the additive is not uniformly distributed within the organic polymer causing problems in the stabilization performance of the additive stabilizer.

In accordance with the present invention an amorphous form of the compound of formula I is obtained which does not suffer the problems associated with the higher melting powder reported previously. This new amorphous form is characterized by a glass transition temperature ($T_g$) within the range of 120°–124° C. as determined by differential scanning calorimetry (DSC). Additionally the amorphous form of the present invention gave a featureless X-ray diffraction pattern obtained using Cu—$K_\alpha$.

Additionally, the new amorphous form of the compound of formula I is more soluble in organic solvents such a lubricating oils, lubricants and in urethanes, prepolymers and the like. The instant amorphous form not only dissolves more rapidly, but also forms compatible solutions in a short time. This is of enormous practical advantage in many end-use applications.

The instant invention also relates to a process for the preparation of this novel amorphous modification of the compound of formula I.

The instant invention also pertains to a composition stabilized against thermal, oxidative and actinic induced degradation which comprises (a) an organic material subject to thermal, oxidative or actinic induced degradation, and (b) an effective stabilizing amount of the amorphous form of 1,1',1"-nitrilo{triethyl-tris-[2,2'-methylene-bis(4,6-di-tert-butylphenyl)] phosphite}, characterized by a glass transition temperature ($T_g$) of 120°–124° C. as determined by differential scanning calorimetry (DSC); and by an X-ray diffraction pattern which is featureless.

The organic material is preferably a polymer processed at elevated temperatures. Particularly preferred organic polymers are the polyolefins, especially polypropylene and polyethylene, and polyamides. Most particularly the organic polymer is polypropylene.

The compound of this invention is a very effective processing stabilizers for polyolefins than the prior art compounds both in preventing molecular weight changes as well as preventing discoloration.

In general polymers which can be stabilized include

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

(a) radical polymerisation (normally under high pressure and at elevated temperature).

(b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/DPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidenenorbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene./isoprene/styrene./ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer, polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins, polyisocyanates or epoxy resins.

26. Crosslinked epoxy resins derived from polyepoxides, for example from bisglycidyl ethers or from cycloaliphatic diepoxides.

27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO.
29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
30. Aqueous emulsions of natural or synthetic rubber, e.g. natural latex or latices of carboxylated styrene/butadiene copolymers.
31. Polysiloxanes such as the soft, hydrophilic polysiloxanes described, for example, in U.S. Pat. No. 4,259,467; and the hard polyorganosiloxanes described, for example, in U.S. Pat. No. 4,355,147.
32. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
33. Radiation curable compositions containing ethylenically unsaturated monomers or oligomers and a polyunsaturated aliphatic oligomer.
34. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.05 to about 3%, and especially 0.05 to about 1%.

The stabilizer of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants
1.1. Alkylated monophenols, for example,
2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
-2($\alpha$-methylcyclohexyl)-4,6-dimethylphenol
2,6-di-octadecyl-4-methylphenol
2,4,6-tri-cyclohexylphenol
2,6-di-tert-butyl-4-methoxymethylphenol
1.2. Alkylated hydroquinones, for example,
2,6-di-tert-butyl-4-methoxyphenol
2,5-di-tert-butyl-hydroquinone
2,5-di-tert-amyl-hydroquinone
2,6-diphenyl-4-octadecyloxyphenol
1.3. Hydroxylated thiodiphenyl ethers, for example,
2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)
1.4. Alkylidene-bisphenols, for example,
2,2'-methylene-bis-(6-tert-butyl-4-methylphenol)
2,2'-methylene-bis-(6-tert-butyl-4-ethylphenol)
2,2'-methylene-bis-[4-methyl-6-($\alpha$-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-($\alpha$-methylbenzyl)-4-nonylphenol]
2,2'-methylene-bis-[6-($\alpha,\alpha$-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl]terephthalate.
1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt 1.6. Acylaminophenols, for example,
  4-hydroxy-lauric acid anilide
  4-hydroxy-stearic acid anilide
  2,4-bis-octylmercapto-6-(3,5-tert-butyl-4-hydroxyanilino)-s-triazine
  octyl-N-(3,5-di-tert-butyl-4-hydroxyphenyl)-carbamate
1.7. Esters of β-(3,5-di-tert-butyl-4-hydroxphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy-3-methylphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid for example,
  N,N'-di-(3,5-di-tert-butyl-4-hydroxyphenylpropionyl)-hexamethylenediamine
  N,N'-di-(3,5-di-tert-butyl-4-hydroxyphenylpropionyl)-trimethylenediamine
  N,N'-di-(3,5-di-tert-butyl-4-hydroxyphenylpropionyl)-hydrazine
1.10 Diarylamines, for example,
  diphenylamine, N-phenyl-1-naphthylamine, N-(4-tert-octylphenyl)-1-naphthylamine,
  4,4'-di-tert-octyl-diphenylamine, reaction product of N-phenylbenzylamine and
  2,4,4-trimethylpentene, reaction product of diphenylamine and 2,4,4-trimethylpentene,
  reaction product of N-phenyl-1-naphthylamine and 2,4,4-trimethylpentene.
2. UV absorbers and light stabilizers
2.1. 2-(2'-Hydroxyphenyl)-benzotriazoles, for example, the
  5'-methyl-,3',5'-di-tert-butyl-,
  5'-tert-butyl-,5'-(1,1,3,3-tetramethylbutyl)-,5-chloro-3',5'-di-tert-butyl-,
  5-chloro-3'-tert-butyl-5'-methyl-,3'-sec-butyl-5'-tert-butyl-,4'-octoxy, 3',5'-di-tert-amyl-, 3',5'-bis-(α,α-dimethylbenzyl),
  3 '-tert-butyl-5'-(2-(omega-hydroxy-octa-(ethyleneoxy) carbonyl-ethyl)-,
  3'-dodecyl-5'-methyl-, and 3'-tert-butyl-5'-(2-octyloxycarbonyl)ethyl-, and
  dodecylated-5'-methyl derivatives.
2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.
2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.
2.4. Acrylates, for example, α-cyano-β,β-diphenylacrylic acid ethyl ester or isooctyl ester, α-carbomethoxycinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.
2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.
2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone), bis(1-octyloxy-2,2,6,6-tetramethylpiperidin-4-yl) sebacate.
2.7. Oxalic acid diamides, for example, 4,4'-di-octyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis (3-dimethylaminopmpyl)-oxalamide, 2-ethoxy-5-tert-butyl-2-ethyloxanilide and its mixture with 2-ethoxy-2-ethyl-5,4-di-tert-butyloxanilide and mixture of ortho-and para-methoxy- as well as of o- and p-ethoxy-disubstituted oxanilides.
2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis [2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.
3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)-hydrazine, 3-salicyloylamino-1,2,4-triazole, bis-benzylidene-oxalic acid dihydrazide.
4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearyl-sorbitol triphosphite, tetrakis-(2,4-di-tert-butylphenyl) 4,4 '-diphenylylenediphosphonite.
5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow mine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

13. Benzofuranones and indolinones, for example those disclosed in U.S. Pat. No. 4,325,863, U.S. Pat. No. 4,338,244 or U.S. Pat. No. 5,175,312, 3-[4-(2-acetoxyethoxy)phenyl]-5,7-di-tert-butyl-benzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one.

The co-stabilizers, with the exception of the benzofuranones listed under 11, are added for example in concentrations of 0.01 to 10%, relative to the total weight of the material to be stabilize.

Further preferred compositions comprise, in addition to components (a) and (b) further additives, in particular phenolic antioxidants, light stabilizers or processing stabilizers.

Particularly preferred additives are phenolic antioxidants (item 1 of the list), sterically hindered amines (item 2.6 of the list), phosphites and phosphonites (item 4 of the list) and peroxide-destroying compounds (item 5.) of the list.

Additional additives (stabilizers) which are also particularly preferred are benzofuran-2-ones, such as described, for example, in U.S. Pat. No. 4,325,863, U.S. Pat. No. 4,338,244 or U.S. Pat. No. 5,175,312.

Examples of such benzofuran-2-ones are compounds of the formula

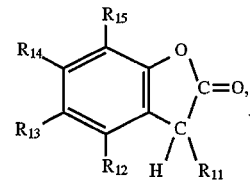

in which $R_{11}$ is phenyl or phenyl which is substituted by 1 to 3 alkyl radicals together having at most 18 carbon atoms, alkoxy having 1 to 12 carbon atoms, alkoxycarbonyl having 2 to 18 carbon atoms or chlorine;

$R_{12}$ is hydrogen;

$R_{14}$ is hydrogen, alkyl having 1 to 12 carbon atoms, cyclopentyl, cyclohexyl or chlorine;

$R_{13}$ has the meaning of $R_{12}$ or $R_{14}$ is a radical of the formula

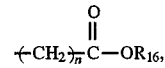

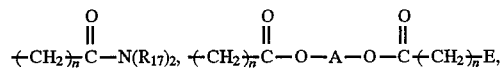

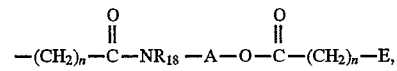

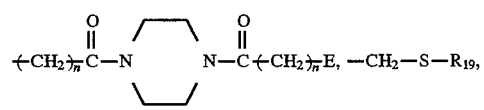

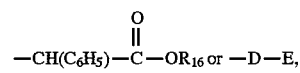

in which $R_{16}$ is hydrogen, alkyl having 1 to 18 carbon atoms, alkyl having 2 to 18 carbon atoms which is interrupted by oxygen or sulfur, dialkylaminoalkyl having a total of 3 to 16 carbon atoms, cyclopentyl, cyclohexyl, phenyl or phenyl which is substituted by 1 to 3 alkyl radicals together having at most 18 carbon atoms;

n is 0, 1 or 2;

the substituents $R_1$, independently of one another, are hydrogen, alkyl having 1 to 18 carbon atoms, cyclopentyl, cyclohexyl, phenyl, phenyl which is substituted by 1 or 2 alkyl radicals together having at most 16 carbon atoms, a radical of the formula —$C_2H_4OH$, —$C_2H_4$—O—$C_mH_{2m+1}$ or

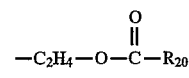

together with the nitrogen atom to which they are attached form a piperidine or morpholine radical;

m is 1 to 18;

$R_{20}$ is hydrogen, alkyl having 1 to 22 carbon atoms or cycloalkyl having 5 to 12 carbon atoms;

A is alkylene having 2 to 22 carbon atoms which may be interrupted by nitrogen, oxygen or sulfur;

$R_{18}$ is hydrogen, alkyl having 1 to 18 carbon atoms, cyclopentyl, cyclohexyl, phenyl, phenyl which is substituted by 1 or 2 alkyl radicals together having at most 16 carbon atoms, or is benzyl;

$R_{19}$ is alkyl having 1 to 18 carbon atoms;

D is —O—, —S—, —SO—, —SO$_2$— or —C($R_{21}$)$_2$—;

the substituents $R_{21}$, independently of one another, are hydrogen, $C_1$-$C_{16}$alkyl, the two $R_{21}$ together containing 1 to 16 carbon atoms, $R_{21}$ is furthermore phenyl or a radical of the formula

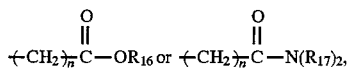

in which n, $R_{16}$ and $R_{17}$ are as defined above;

E is a radical of the formula

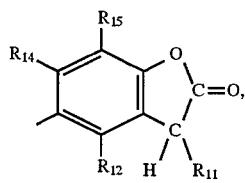

in which $R_{11}$, $R_{12}$ and $R_{14}$ are as defined above; and $R_{15}$ is hydrogen, alkyl having 1 to 20 carbon atoms, cyclopentyl, cyclohexyl, chlorine or a radical of the formula

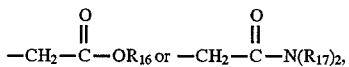

in which $R_{16}$ and $R_{17}$ are as defined above, or $R_{15}$ together with $R_{14}$ forms a tetramethylene radical.

Preference is given to those benzofuran-2-ones in which $R_{13}$ is hydrogen, alkyl having 1 to 12 carbon atoms, cyclopentyl, cyclohexyl, chlorine or a radical of the formula

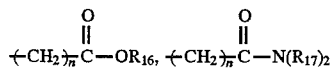

or —D—E, in which n, $R_{16}$, $R_{17}$, D and E are as defined above, $R_{16}$ is in particular hydrogen, alkyl having 1 to 18 carbon atoms, cyclopentyl or cyclohexyl.

Preference is given furthermore to those benzofuran-2-ones in which $R_{11}$ s phenyl or phenyl which is substituted by 1 or 2 alkyl radicals together having at most 12 carbon atoms; $R_{12}$ is hydrogen; $R_{14}$ is hydrogen or alkyl having 1 to 12 carbon atoms; $R_{13}$ is hydrogen, alkyl having 1 to 12 carbon atoms,

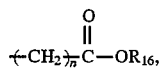

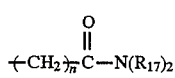

or —D—E; $R_{15}$ is hydrogen, alkyl having 1 to 20 carbon atoms,

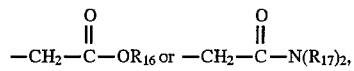

$R_{15}$ together with $R_{14}$ forms a tetramethylene radical, n, $R_{16}$, $R_{17}$, D and E being as defined at the beginning.

Of particular interest are also those benzofuran-2-ones in which $R_{11}$ is phenyl; $R_{13}$ is hydrogen, alkyl having 1 to 12 carbon atoms or —D—E; $R_{12}$ and $R_{14}$, independently of one another, are hydrogen or alkyl having 1 to 4 carbon atoms; and $R_{15}$ is alkyl having 1 to 20 carbon atoms, D and E being as defined at the beginning.

Of special interest are finally also those benzofuran-2-ones in which $R_{11}$ is phenyl; $R_{13}$ is alkyl having 1 to 4 carbon atoms or —D—E; $R_{12}$ and $R_{14}$ are hydrogen; and $R_{15}$ is alkyl having 1 to 4 carbon atoms, cyclopentyl or cyclohexyl, D being a group —C($R_{21}$)$_2$— and E being a radical of the formula

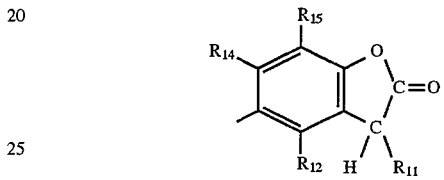

the substituents $R_{21}$ being identical to or different from one another and each being alkyl having 1 to 4 carbon atoms, and $R_{11}$, $R_{12}$, $R_{14}R_{15}$ being as defined.

The amount of additional additives, in particular stabilizers, for example of the benzofuran-2-ones mentioned, can vary within wide limits. For example, 0.0005 to 10, preferably 0.001 to 5, in particular 0.01 to 2, % by weight thereof can be present in the compositions according to the invention.

Incorporation of the amorphous form of 1,1',1"-nitrilo{triethyl-tris-[2,2'-methylene-bis(4,6-di-tert-butylphenyl)] phosphite} and, if desired, further additives in the polymer organic material is carried out by known methods, for example before or during moulding or by applying the dissolved or dispersed compounds to the polymer organic material, if appropriate with subsequent slow evaporation of the solvent. The amorphous modification according to the invention can also be added to the materials to be stabilized in the form of a masterbatch containing them, for example, in a concentration of 2.5 to 25% by weight The amorphous modification according to the invention can also be added before or during polymerization or before crosslinking.

The amorphous modification according to the invention can be incorporated in the material to be stabilized in pure form or encapsulated in waxes, oils or polymers.

The amorphous modification according to the invention can also be sprayed onto the polymer to be stabilized. They are capable of diluting other additives (for example the abovementioned customary additives) or their melts, thus enabling them to be sprayed onto the polymer to be stabilized also together with these additives. Addition by spraying during deactivation of the polymerization catalysts is particularly advantageous, it being possible, for example, for the steam used for deactivation to be used for spraying.

In the case of bead polymerized polyolefins, it may be advantageous, for example, to apply the amorphous modification according to the invention, if desired together with other additives, by spraying.

The materials thus stabilized can be used in a wide range of forms, for example as films, fibres, tapes, moulding compositions, profiles or as binders for paints, adhesives or cements.

As already mentioned, the organic materials to be protected are preferably organic, in particular synthetic, polymers. Of these, the materials being protected are particularly advantageously thermoplastic materials, in particular polyolefins. The excellent efficiency of the amorphous form of 1,1',1"-nitrilo{triethyl-tris-[2,2'-methylene-bis(4,6-di-tert-butylphenyl)]phosphite} as a processing stabilizer (thermal stabilizer) should be mentioned in particular. To this end, it is advantageously added to the polymer before or during its processing. It is however also possible to stabilize other polymers (for example elastomers) or lubricants or hydraulic fluids against degradation, for example light-induced or thermal-oxidative degradation. For elastomers, see the above list of possible organic materials.

Suitable lubricants and hydraulic fluids are based, for example, on mineral or synthetic oils or mixtures thereof. Lubricants are known to one skilled in the art and described in the relevant technical literature, for example in Dieter Klamann, "Schmierstoffe und verwandte Produkte" (Verlag Chemie, Weinheim 1982), in Schewe-Kobek, "Das Schmiermittel-Taschenbuch" (Dr. Alfred Hüthig-Verlag, Heidelberg, 1974) and in "Ullmanns Enzyklopädie der technischen Chemie" vol. 13, pages 85–94 (Verlag Chemie, Weinheim, 1977).

Accordingly, a preferred embodiment of the present invention is the process of using the amorphous form of 1,1',1"-nitrilo{triethyl-tris-[2,2'-methylene-bis(4,6-di-tert-butylphenyl)]phosphite} for stabilizing organic materials against oxidative, thermal or light-induced degradation.

The amorphous modification according to the invention is preferably used as processing stabilizer (thermal stabilizer) of thermoplastic polymers.

The present invention also provides a process for stabilizing an organic material against oxidative, thermal or light-induced degradation, which comprises incorporating therein or applying thereto the amorphous form of 1,1',1"-nitrilo{triethyl-tris-[2,2'-methylene-bis(4,6-di-tert-butylphenyl)]phosphite}.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinnammate ), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctaraethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris-[2-(3,5-di-tert-butyl-4-hydroxyhydrocinnamoyloxy) ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis-(4,6-di-tert-butylphenol).

The hindered amine compound of particular interest is selected from the group consisting of bis(2,2,6,6-tetramethylpiperidin-4-yl)sebacate, bis(1,2,2,6,6-pentamethylpiperidin-4-yl)sebacate, di(1,2,2,6,6-pentamethylpiperidin-4-yl)(3,5-di-tert-butyl-4-hydroxybenzyl)butylmalonate, 4-benzoyl-2,2,6,6-tetramethylpiperidine, 4-stearyloxy-2,2,6,6-tetramethylpiperidine, 3-n-octyl-7,7,9,9-tetramethyl-1,3,8-triaza-spiro[4.5]decane-2,4-dione, tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2]heneicosane, polycondensation product of 2,4-dichloro-6-tert-octylamino-s-triazine and 4,4'-hexamethylenebis (amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N",N"'-tetrakis[(4,6-bis-(butyl-2,2,6,6-tetramethyl-piperidin-4-yl)-amino-s-triazin-2-yl]-1,10-diamino-4,7-diazadecane, mixed [2,2,6,6-tetramethylpiperidin-4-yl/β,β,β',β'-tetramethyl- 3,9-(2,4,8,10-tetraoxaspiro[5.5]-undecane) diethyl]1,2,3,4-butanetetracarboxylate, mixed [1,2,2,6,6-pentamethylpiperidin-4-yl/β,β,β',β'-tetramethyl-3,9-(2,4,8,10-tetraoxaspiro[5.5]undecane)diethyl]1,2,3,4-butanetetracarboxylate, octamethylene bis(2,2,6,6-tetramethylpiperidin-4-carboxylate), 4,4'-ethylenebis(2,2,6,6-tetramethylpiperazin-3-one), and bis(1-octyloxy-2,2,6,6-tetramethylpiperidin-4-yl) sebacate.

A most preferred hindered amine compound is bis(2,2,6,6-tetramethylpiperidin-4-yl) sebacate, the polycondensation product of 1-(2-hydroxyethyl)-2,2,6,6-tetramethyl-4-hydroxypiperdine and succinic acid, the polycondensation product of 2,4-dichloro-6-tert-octylamino-s-triazine and 4,4'-hexamethylenebis(amino-2,2,6,6-tetramethylpiperidine), N,N',N",N"'-tetrakis[(4,6-bis(butyl-(2,2,6,6-tetramethylpiperidin-4-yl)amino)-s-triazine-2-yl]-1,10-diamino-4,7-diazadecane or bis(1-octyloxy-2,2,6,6-tetramethylpiperidin-4-yl) sebacate.

The lubricating oil may be a mineral oil, a synthetic oil or any mixture of such oils. Mineral oils are preferred and examples of these include paraffinic hydrocarbon oils e.g. a mineral oil having a viscosity of 46 mm$^2$/s at 40° C.; "150 Solvent Neutral" a solvent refined neutral mineral oil having a viscosity of 32 mm$^2$/s at 40° C.; and "solvent brightstocks", a high boiling residue from the process of refining mineral oil, and having a viscosity of 46 mm$^2$/s at 40° C.

Synthetic lubricating oils which may be present may be synthetic hydrocarbons such as polybutenes, alkyl benzenes and poly-alpha olefins as well as simple di-, tri- and tetra-esters, complex esters and polyesters derived from carboxylic acid esters of formula: $G_1$-OCC-alkylene-COO$G_2$ wherein "alkylene" denotes an alkylene residue having from 2 to 14 carbon atoms and $G_1$ $G_2$ are the same or different and each is an alkyl group having from 6 to 18 carbon atoms. Tri-esters which are of use as lubricating oil base stocks are those derived from trimethylolpropane and $C_6$–$C_{18}$ mono-carboxylic acids or mixtures thereof, whereas suitable tetra-esters include those derived from pentaerythritol and a $C_6$–$C_{18}$ mono-carboxylic acid or mixtures thereof.

Complex esters suitable for use as components of the composition of the present invention are those derived from monobasic acids, dibasic acids and polyhydric alcohols, for instance the complex ester derived from trimethylol propane, caprylic acid and sebacic acid.

Suitable polyesters are those derived from any aliphatic dicarboxylic acid having from 4 to 14 carbon atoms and at least one aliphatic dihydric alcohol having from 3 to 12 carbon atoms, e.g. those derived from azelaic acid or sebacic acid and 2,2,4-trimethylhexane-1,6-diol.

Other lubricating oils are those known to the art-skilled and described e.g. in Schewe-Kobek, "Schmiermittel-Taschenbuch", (Huethig Verlag, Heidelberg 1974), and in D. Klamarm, "Schmierstoff und verwandte Produkte", (Verlag Chemic, Weinheim 1982).

The lubricating oils applicational media can also contain other additives which may be added to improve the basic properties of lubricants e.g. metal passivators, viscosity-index improvers, pour-point depressants, dispersing agents, detergents, additional rust inhibitors, extreme pressure additives, anti-wear additives and antioxidants.

Examples of phenolic antioxidants

1. Alkylated Monophenols 2,6-Di-tert-butyl-4-methylphenol,2,6-di-tert-butylphenol, 2-tert-butyl-4,6-dimethylphenol,2,6-di-tert-butyl-4-ethyl-phenol,2,6-di-tert-butyl-4-n-butylphenol,2,6-di-tert-butyl-4-i-butylphenol,2,6-di-cyclopentyl-4-methylphenol,2-(β-methylcyclohexyl)-4,6-dimethylphenol,2,6-di-octa-decyl-4-methylphenol,2,4,6-tri-cyclohexylphenol, 2,6-di-tert-butyl-4-methoxymethylphenol, o-tert-butylphenol.

2. Alkylated Hydroquinones 2,6-Di-tert-butyl-4-methoxyphenol,2,5-di-tert-butyl-hydroquinone,2,5-di-tert-amyl-hydroquinone, 2,6-diphenyl-4-octa-decyloxyphenol.

3. Hydroxylated Thiodiphenylethers 2,2'-Thio-bis-(6-tert-butyl-4-methylphenol),2,2'-thio-bis-(4-octyl-phenyl), 4,4'-thio-bis-(6-tert-butyl-3-methylphenol),4,4'-thio-bis-(6-tert-butyl-2-methylphenol).

4. Alkylidene-Bisphenols 2,2'-Methylene-bis-(6-tert-butyl-4-methylphenol), 2,2'-methylene-bis-(6-tert-butyl-4-ethylphenol), 2,2'-methylene-bis-(4-methyl-6-(α-methyl-cyclohexyl)-phenol), 2,2'-methylene-bis-(4-methyl-6-cyclohexylphenol), 2,2'-methylene-bis-(6-nonyl-4-methylphenol), 2,2'-methylene-bis-(4,6-di-tert-butylphenol), 2,2'-ethylidene-bis-(4,6-di-tert-butylphenol), 2,2'-ethylidene-bis-(6-tert-butyl-4- or-5-isobutylphenol), 2,2'-methylene-bis-(6-(α-methylbenzyl-4-nonylphenol), 2,2-methylene-bis-(6-(α,α-di-methylbenzyl)-4-nonylphenol), 4,4'-methylene-bis-(2,6-di-tert-butyl-phenol), 4,4'-methylene-bis-(6-tert-butyl-2-methylphenol), 1,1-bis-(5-tert-butyl-4-hydroxy-2-methyl-phenol)-butane, 2,6-di-(3-tert-butyl-5-methyl-2-hydroxy-benzyl)-4-methylphenol, 1,1,3-tris-(5-tert-butyl-4-hydroxy-2-methylphenyl)-3-n-dodecyl)-mercaptobutane, ethyleneglycol-bis-[3,3-bis-(3'-tert-butyl-4'-hydroxyphenyl)-butyrate], bis-(3-tert-butyl-4-hydroxy-5-methylphenyl)-dicyclopentadiene, bis-[2-(3'-tert-butyl-2'-hydroxy-5'-methyl-benzyl)-6-tert-butyl-,4-methyl-phenyl]-terephthalate.

5. Benzyl Compounds 1,3,5-Tri-(3,5-di-tert-butyl-4-hydroxybenzyl)-2,4,6-trimethyl-benzene, bis(3,5-di-tert-butyl-4-hydroxybenzyl)-sulfide, 3,5-di-tert-butyl-4-hydroxybenzyl-mercaptoacetic acid-isooctylester, bis-(4-tert-butyl-3-hydroxy-2,6-dimethyl-benzyl)dithiolterephthalate, 1,3,5-tris-(3,5-di-tert-butyl-4-hydroxybenzyl)-isocyanurate, 1,3,5-tris-(4-tert-butyl-3-hydroxy- 2,6-dimethylbenzyl)-isocyanurate, 3,5-di-tert-butyl-4-hydroxybenzyl-phosphonic acid-dioctadecylester, 3,5-di-tert-butyl-4-hydroxybenzyl-phosphonic acid-monoethylester, calcium-salt.

6. Acylaminophenols

4-Hydroxy-lauric acid anilide, 4-hydroxy-stearic acid anilide, 2,4-bis-octylmercapto-6-(3,5-di-tert-butyl-4-hydroxyanilino)-s-triazine, N-(3,5-di-tert-butyl-4-hydroxyphenyl)-carbamic acid octyl ester.

7. Esters of β-(3,5Di-tert-butyl-4-hydroxyphenl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate, thiodiethylene glycol, bis-hydroxyethyl-oxalic acid diamide.

8. Esters of β-(5-tert-butyl-4-hydroxy-3-methylphenyl)-propionic acid with mono- or polyhydric alcohols, for example with methanol, isooctyl alcohol, 2-ethylhexanol, diethylene glycol, octadecanol, triethylene glycol, 1,6-hexanediol, pentaerythritol, neopentyl glycol, tris-hydroxyethyl isocyanurate,thiodiethylene glycol, di-hydroxyethyl-oxalic acid diamide.

9. Amides of β-(3,5-Di-tert-butyl-4-hydroxyphenyl)-propionic acid for example N,N'-Bis-(3,5-di-tert-butyl-4-hydroxyphenylpropionyl)-hexamethylenediamine, N,N'-bis-(3,5-di-tert-butyl-4-hydroxy-phenylpropionyl)-trimethylene-diamine, N,N'-bis(3,5-di-tert-butyl-4-hydroxyphenylpropionyl)-hydrazine.

Examples of amine antioxidants:

N,N'-Di-isopropyl-p-phenylenediamine, N,N'-di-sec.-butyl-p-phenylenediamine, N,N'-bis(1,4-dimethyl-pentyl)-p-phenylenediamine, N,N'-bis(1-ethyl-3-methyl-pentyl)-p-phenylenediamine, N,N'-bis(1-methyl-heptyl)-p-phenylenediamine, N,N'-dicyclohexyl-p-phenylenediamine, N,N'-diphenyl-p-phenylenediamine, N,N'-di-(naphthyl-2-)-p-phenylenediamine, N-isopropyl-N'-phenyl-p-phenylenediamine, N-(1,3-dimethylbutyl)-N'-phenyl-p-phenylenediamine, N-(1-methyl-heptyl)-N'-phenyl-p-phenylenediamine, N-cyclohexyl-N'-phenyl-p-phenylenediamine, 4-(p-toluene-sulfonamido) diphenylamine, N,N'-dimethyl-N,N'-di-sec-butyl-p-phenylenediamine, di-phenylamine, N-allyldiphenylamine, 4-isopropoxy-diphenylamine, N-phenyl-1-naphthylamine, N-phenyl-2-naphthylamine, octylated diphenylamine, e.g. p,p'-di-tert-octyldiphenylamine, 4-n-butylaminophenol, 4-butyrylamino-phenol, 4-nonanoylamino-phenol, 4-dodecanoylamino-phenol, 4-octadecanoyl-amino-phenol, di-(4-methoxy-phenyl)-amine, 2,6-di-tert-butyl-4-dimethyl-amino-methyl-phenol, 2,4'-diamino-diphenylmethane, 4,4'-diaminodiphenyl-methane, N,N,N',N'-tetramethyl-4,4'-diamino-diphenylmethane, 1,2-di-(phenyl-amino)-ethane, 1,2-di-[2-methyl-phenyl)-amino]-ethane, 1,3-di-(phenylamino)-propane, (o-tolyl)-biguanide, di-[4-1',3'-dimethyl-butyl)-phenyl]amine, tert-octylated N-phenyl-1-naphthylamine, mixture of mono- and dialkylated tert-butyl-/tert-octyldiphenylamines, 2,3-dihydro-3,3-dimethyl-4H-1, 4-benzothiazine, phenothiazine, N-allylphenothiazine, tert-octylated phenothiazine, 3,7-di-tert-octylphenothiazine.

Examples for other antioxidants:

Aliphatic or aromatic phosphites, esters of thiodipropionic acid or of thiodiacetic acid, or salts of dithiocarbamic or dithiophosphoric acid.

Examples of metal passivators, for example for copper, are:

Triazoles, benzotriazoles and derivatives thereof, tolutriazole and derivatives thereof, e.g. di(2-ethylhexyl)-aminomethyltolutriazole, 2-mercaptobenzothiazole, 5,5'-methylene-bis-benzotriazole, 4,5,6,7-tetrahydrobenzotriazole, salicyclidene-propylene-diamine and salicyclamino-guanidine and salts thereof, 1,2,4-triazole and N,N'-disubstituted aminomethyl triazoles of formula

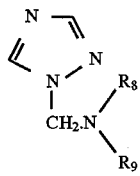

in which $R_8$ and $R_9$ are, independently, e.g. alkyl, alkenyl, or hydroxyethyl, obtained by reacting 1,2,4-triazole with formaldehyde and an amine, $HNR_8R_9$, as disclosed in European Patent Application No. 160620; and the Mannich reaction products derived from benzotriazole or tolutriazole, formaldehyde and an amine $HNR_8R_9$.

Examples of rust inhibitors are:

a) Organic acids, their esters, metal salts and anhydrides, e.g. N-oleoyl-sarcosine, sorbitan-mono-oleate, lead-naphthenate, alkenyl-succinic acids and -anhydrides, e.g. dodecenyl-succinic acid anhydride, succinic acid partial esters and amines, 4-nonyl-phenoxy-acetic acid.

b) Nitrogen-containing compounds, e.g.

I. Primary, secondary or tertiary aliphatic or cycloaliphatic amines and amine-salts of organic and inorganic acids, e.g. oil-soluble alkyl-ammonium carboxylates II. Heterocyclic compounds, e.g. substituted imidazolines and oxazolines.

c) Phosphorus-containing compounds, e.g. amine salts of phosphonic acid or phosphoric acid partial esters, zinc dialkyldithio phosphates.

d) Sulfur-containing compounds, e.g. barium-dinonylnaphthalene-n-sulfonates, calcium petroleum sulfonates.

e) Derivatives of gamma-alkoxypropylamines described in Japanese Patent Publication No. 15783/1973; and f) Salts having the formula $Y$—$NH_3$—$R_{10}CO_2$— in which Y is a group $R_{11}X_1CH_2CH(OH)$ $CH_2$ in which $R_{10}$ and $R_{11}$, independently, are e.g. alkyl and $X_1$ is $O,CO_2,NH$, N(alkyl), N(alkenyl) or S, these salts being prepared by mixing an amine $Y$-$NH_2$ with an acid $R_{10}CO_2H$, as disclosed in DE-OS 3437 876 (German Offenlegungsschrift).

g) Compounds having the formula

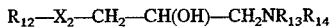

in which $X_2$ is —O—, —S—, —$SO_2$—C(O)—O— or —N(Rd) in which $R_{12}$ is H or $C_1$–$C_{12}$ alkyl, $R_{13}$ is unsubstituted $C_1$–$C_4$alkyl or $C_2$–$C_5$alkyl substituted by one to three hydroxyl groups, $R_{14}$ is hydrogen, unsubstituted $C_1$–$C_4$alkyl or $C_2$–$C_5$alkyl substituted by one to three hydroxyl groups provided that at least one, of $R_{13}$ and $R_{14}$ is hydroxy-substituted, and $R_{12}$ is $C_2$–$C_{20}$alkyl —$CH_2$—CH (OH)—$CH_2NR_{13}R_{14}$ or $R_{12}$ is $C_2$–$C_{18}$alkenyl, $C_2$–$C_3$alkynyl or $C_5$–$C_{12}$cycloalkyl provided that, when $X_2$ is —O— or —C(O)—O—, $R_{12}$ is branched $C_4$–$C_{20}$alkyl. These compounds are described in GB Patent Specification 2172284A.

h) Compounds having the formula:

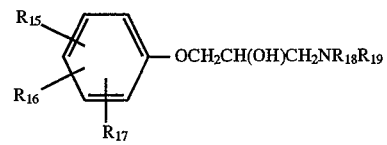

in which $R_{15}$, $R_{16}$, $R_{17}$ are, independently, hydrogen, $C_1$–$C_{15}$alkyl, $C_5$–$C_{12}$cycloalkyl, $C_6$–$C_{15}$aryl or $C_7$–$C_{12}$aralkyl and $R_{18}R_{19}$, independently, are hydrogen, 2-hydroxyethyl or 2-hydroxypropyl, provided that $R_{18}$ and $R_{19}$ are not simultaneously hydrogen and, when $R_{18}$ and $R_{19}$ are each —$CH_2CH_2OH$, $R_{15}$ and $R_{16}$ are not Simultaneously hydrogen and $R_{17}$ is not pentyl. These compounds are described in EP Patent specification 0 252 007.

Examples of viscosity-index improvers are: Polyacrylates, polymethacrylates, vinylpyrrolidone/methacrylate-copolymers, polyvinylpyrrolidones, polybutanes, olefin-copolymers, styrene/-acrylate-copolymers, polyethers.

Examples of pour-point depressants are: Polymethacrylates, alkylated naphthalene derivatives.

Examples of dispersants/detergents are: Polybutenylsuccinic acid-amides or-imides, polybutenyl-phosphonic acid derivatives, basic magnesium-, calcium-, and bariumsulfonates and -phenolates.

Examples of anti-wear additives and extreme pressure additives are: Sulphur- and/or phosphorus- and/or halogen-containing compounds e.g. sulphurised vegetable oils, zinc dialkyldithiophosphates, tritolylphosphate, chlorinated paraffins, alkyl- and aryldi- and trisulphides, triphenylphosphorothionate.

The process for the preparation of the instant amorphous modification of the compound of formula I comprises heating a melt of any of the solid forms of the compound of formula I and rapidly cooling the melt. The preferred method consists of pouring the molten material onto a cool surface maintained below 100° C., more preferably near 25° C. The amorphous solid thus obtained may be further ground or granulated into any desired particle size by conventional means.

The present invention also provides a process for stabilizing an organic material against oxidative, thermal or light-induced degradation, which comprises incorporating therein or applying thereto the new amorphous form of 1,1',1"-nitrilo{triethyl-tris-[2,2'-methylene-bis(4,6-di-tert-butylphenyl)]phosphite}.

Differential scanning calorimetry (DSC) measurements are obtained on a TA Instrument Inc., 910 differential scanning calorimeter, with a 100 mL/min nitrogen purge, aligned aluminum pan, temperature scan at 5° C./min to 350° C.

X-ray diffraction patterns are recorded on a Philips Norelco X-ray Diffractometer unit, using Cu—$K_\alpha$ radiation with a nickel filter.

EXAMPLE 1

The compound of formula I, 1,1',1"-nitrilo{triethyl-tris-[2,2'-methylene-bis(4,6-di-tert-butylphenyl)]phosphite}, is prepared according to procedure of Example 3 of U.S. Pat. No. 4,318,845. The product obtained is heated at 200° C. until a clear melt is obtained. The melt is cooled rapidly to ambient temperature to yield a glassy solid with a $T_g$(DSC) of 120°–124° C. The white solid is conveniently found into a white powder using a mortar and pestle. The X-ray diffraction pattern obtained using Cu—$K_\alpha$ for the instant amorphous compound is featureless whereas the prior an compound of Example 3 of U.S. Pat. No. 4,318,845 shows a crystalline pattern clearly different from the featureless pattern found for the instant amorphous compound.

EXAMPLE 2

Bulk Density

This example illustrates the superior packaging properties of the novel amorphous solid modification of the compound of formula I as prepared in Example 1 as compared to the powder form of the compound of Example 3 of U.S. Pat. No. 4,318,845.

The apparent bulk density of the solids is measured according to the method of ASTM D-1895 (79). A higher apparent bulk density allows for a greater mass per unit volume which affords advantages in packaging of the solid product, such as lower costs for the packaging material, less storage space is required, etc.

| Compound of | Bulk Density (g/mL) |
| --- | --- |
| Example 1 (amorphous solid form) | 0.43 |
| Example 3 of U.S. 4,318,845 (prior art) | 0.33 |

The instant amorphous solid form prepared in Example 1 has a much higher bulk density than the prior art compound of Example 3 of U.S. Pat. No. 4,318,845 with its concomitant superior packaging properties.

EXAMPLE 3

Process Stabilization of Polypropylene at 525° F. (274° C.)

The blank formation comprises unstabilized polypropylene (PROFAX 6501, Himont) containing 0.075% by weight of calcium stearate. The test additives are incorporated into the polyproyplene by dry blending or, when the additive is a liquid, using a minimum amount of methylene chloride solvent. The solvent is then removed by evaporation under reduced pressure. The stabilized resin formulation is extruded at 90 rpm from a 1 inch (2.54 cm) diameter extruder at 525° F. (274° C/) with a residence time of 90 seconds. After each of the first, third and fifth extrusions, the melt flow rate (in grams/10 minutes) is determined by ASTM method D 1238 on the pellets obtained from the extruder.

The instant compound is effective in stabilizing polypropylene against thermal and oxidative degradation as shown by a minimum change in the melt flow rate in the presence of a representative phenolic antioxidant and is essentially as effective as the prior art compound of U.S. Pat. No. 4,318, 845.

Pellets obtained after the first, third and fifth extrusions are compression molded into 125 mil (3.2 mm) plaques at 450° F. (232° C.) and the yellowness index (YI) values are determined according to ASTM method D 1925. Lower YI values indicate less discoloration.

The instant compound is effective in stabilizing polypropylene against discoloration as shown by a minimum change in the yellowness index in the presence of a representative phenolic antioxidant and is essentially as effective as the prior an compound of U.S. Pat. No. 4,318,845.

EXAMPLE 4

Solubility in Lubricating Oil

The following experiments are performed to determine the solubility of amorphous compound A and prior an compound B in Mobil BB oil. Both compounds have the same uniform particle sizes (40–70 micron).

Compounds Tested

Compound A=amorphous form of 1,1',1"-nitrilo{triethyl-tris-[2,2'-methylene-bis(4,6-di-tert-butylphenyl)]phosphite}, prepared in accordance with instant Example 1.

Compound B=powder form of 1,1',1"-nitrilo{triethyl-tris-[2,2'-methylene-bis(4,6-di-tert-butylphenyl)]phosphite}, prepared in accordance with Example 3 of U.S. Pat. No. 4,318,845.

Test Procedure and Results

Experiment 4a

Into a vial of 980 mg. of Mobil BB oil is added 20 mg. of compound A at ambient temperature. For the first 60 minutes, the vial is shaken every 15 minutes. After the initial 60 minutes, the vial is left standing. All of compound A dissolves into the oil after hours to give a clear solution.

Experiment 4b

Into a vial of 980 mg. of Mobil BB oil is added 20 mg. of compound B at ambient temperature. For the first 60 minutes, the vial is shaken every 15 minutes. After the initial 60 minutes, the vial is left standing. After 3 hours, compound B gives a cloudy suspension.

Experiment 4c

Into a vial of 980 mg. of Mobil BB oil is added 20 mg. of compound A at ambient temperature. The vial is then placed into a 60° C. oil bath. After 20 minutes, all of compound A dissolves into the oil to give a clear solution.

Experiment 4d

Into a vial of 980 mg. of Mobil BB oil is added 20 mg. of compound B at ambient temperature. The vial is then placed into a 60° C. oil bath. After 20 minutes, compound B gives a cloudy suspension.

| Exp. # | % by weight Test Compound | Temp. | Observation | Time |
| --- | --- | --- | --- | --- |
| 4a | 2% A | RT | Clear solution | 3 hrs. |
| 4b | 2% B | RT | Cloudy Suspension | 3 hrs. |
| 4c | 2% A | 60° C.* | Clear solution | 20 min. |
| 4d | 2% B | 60° C.* | Cloudy suspension | 20 min. |

*The temperature reading is the oil bath temperature.

In summary, the instant amorphous Compound A shows a faster rate of dissolving and better solubility in lubricants as compared to the prior art powder form Compound B. This provides better compatibility and more uniform distribution of the instant compound with an organic material during formulation compared to the prior art compound.

EXAMPLE 5

Solubility in LLDPE Film at Various Temperatures

Experiments are carried out to determine the solubility of the instant compound into linear low density polyethylene (LLDPE) films at 20° C., 40° C. and 60° C. by diffusion-in of a relatively homogeneous particle size (<70 microns) of the test sample suspended in silicon oil.

Each sample is carefully ground with a mortar and pestle and the particle size below 70 microns is separated by sieving with a 200 mesh screen. The powder is then suspended in silicon oil (polydimethylsiloxane, L-45, Union Carbide Chemicals) at a concentration of approximately 38% (wt/wt). A few drops of this suspension is placed on a 10 mil (0.254 mm) thick, 2"×2" (5.08 cm ×5.08 cm) compression molded film and a second film of the same dimension is placed on top. The films are gently pressed together so that the suspension forms a thin liquid layer between the polymer films. Excess suspension is removed and the procedure is repeated till a stack of eight films (six films for evaluation) are prepared. The stack is then placed between two 2.5"×2.5" (6.35 cm ×6.35 cm) ceramic tiles and wrapped in aluminum foil and held together with a G-clamp. Each stack is aged at 20° C., 40° C. and 60° C. under a nitrogen atmosphere. At specified intervals, a single film is removed from the stack and the excess suspension is washed from the film with hexane. The film is then analyzed by X-ray fluorescence for total phosphorus content LLDPE containing 0, 1000 ppm and 2000 ppm of the test compound are used as standard controls for this X-ray fluorescence method.

The instant amorphous compound of Example 1 is more soluble in LLDPE than is the prior an compound of Example 3 of U.S. Pat. No. 4,318,845.

EXAMPLE 6

Stabilization of Unsaturated Elastomer

The instant compound of Example 1 is evaluated in an emulsion of SBR (cold polymerized, 23.5% styrene with a 52 Mooney Viscosity). The unstabilized SBR (60 g) is added to the mixing chamber of a Brabender Plasticorder set at 150° C. and 60 rpm. After 30 seconds, 0.5% by weight of the compound of instant Example 1 is added to the chamber. Stability of the SBR is determined by the time until onset of crosslinking of the rubber as indicated by an increase in the torque curve. The sample stabilized by the instant compound has a longer induction time till crossing occurs than does the unstabilized SBR.

EXAMPLE 7

Stabilization of Polyol

A premix of 10 g of water, 0.25 g of triethylenetetramine, 2 g of L-5740 (silicone surfactant, Union Carbide) and 20 g of ANTIBLAZE® AB-100 (chlorinated aromatic flame retardant, Albright & Wilson) is added to 200 g of 3000 molecular weight polyether polyol containing the stabilizer package listed below*. The mixture is stirred for five minutes with a high speed Lightning Mixer. Then 0.4 g of stannous octoate is added and the mixture is stirred for 5 seconds. Finally, 125 g of toluene diisocyanate (80% 2,6-isomer;, 20% 2,4-isomer) is added. The mixture is stirred for 7 seconds at high speed mixing and is then poured into a 10"×10"×5" (25.4 cm ×25.4 cm ×12.7 cm) cardboard box. The foam is allowed to rise completely. After standing 5 minutes, the box is removed and the sample cured in a microwave over for five minutes at 50% power. The foam is then immediately air over cured at 125° C. for three minutes. The foams are then cut in half for visual assessment of discoloration or scorch. *Stabilizer package:

Control is 2,6-di-tert-butyl-4-methylphenol (BHT) 2000 ppm; and NAUGARD® 445 (diphenylamine antioxidant, Uniroyal) 2000 ppm.

Instant package is the above plus 1000 ppm of the compound of Example 1.

Visual inspection of the two foams shows that the foam containing the instant stabilizer package with the compound of Example 1 present is less discolored than the foam stabilized with the control stabilizer package. The instant compound demonstrates better scorch protection.

EXAMPLE 8

Stabilization of Polycarbonate

Additive free bisphenol A polycarbonate (LEXAN® 141-111N, General Electric) is dried and blended with 0.3 weight percent of a benzotriazole UV absorber (TINUVIN® 329, Ciba-Geigy) and 0.08 weight percent of instant compound of Example 1. The mixture is extruded and pelletized at 550° F. (288° C.) on a 1" (2.54 cm) single screw extruder. Injection molded plaques (2"×2"×125 mil; 5.08 cm ×5.08 cm ×3.175 mm) are prepared in a BOY 30M injection molder at 560° F. (293° C.) with a mold temperature of 150° C. The resulting plaques are measured for yellowness index (YI) using ASTM D 1925-70. The plaques containing the instant compound of Example 1 have a lower YI values than those containing the UV absorber alone demonstrating the better performance achieve by the concomitant presence of the instant phosphite.

EXAMPLE 9

Stabilization of Poly(ethylene terephthalate)

Poly(ethylene terephthalate), PET (KODAPAR®7352, Eastman Chemical) is tumble blended with 0.5% by weight of the compound of instant Example 1. The polymer is then extruded and pelletized at 500° F. (260° C.) in a MPM 1" (2.54 cm) single screw extruder. The pellets are collected, redried and reextruded 5 times. Pellets are collected from each extrusion pass and the polymer intrinsic viscosity measured. PET containing the instant compound of Example 1 shows a higher retention of original intrinsic viscosity through the five extrusion passes than does PET containing no stabilizer.

EXAMPLE 10

Stabilization of Poly(butylene terephthalate)

Poly(butylene terephthalate), PBT (RYNITE® 9160, DuPont) is tumble blended with 0.3% by weight of the compound of instant Example 1. The polymer is then extruded and pelletized at 260° C. A portion of the collected pellets are reextruded under the same conditions for a second pass. The remainder from the first extrusion is injection molded into 2"×2"×125 mil (5.08 cm ×5.08 cm ×3.175 mm) plaques at 540° F. (282° C.) with a 100° C. mold temperature in a BOY 30M molder. Intrinsic viscosities of the second pass extrudate and the injection molded plaques are determined. The PBT containing the instant compound of Example 1 shows a better retention of intrinsic viscosity value than does PBT containing no stabilizer.

The plaques are measured for yellowness index (color) using ASTM D 1925-70. The plaques containing the instant compound of Example 1 have a lower YI values (less discoloration) than do the plaques prepared from the control unstabilized PBT.

EXAMPLE 11

Stabilization of 6,6-Nylon 6,6-Nylon (ZYTEL® 101, DuPont) is thoroughly dried in a vacuum oven and tumble blended with 0.5% by weight of the compound of instant Example 1. The polyamide is extruded on a 1" (2.54 cm) MPM extruder at 575° F. (302° C.). The collected pellets are injection molder at 575° F. (302° C.) with the mold at 150° C. in a BOY 30M injection molder. The plaques obtained are measured for yellowness index (YI) values using ASTM D 1925-70. The plaques containing the instant compound of Example 1 exhibit lower YI values (less discoloration) than do the unstabilized control plaques.

EXAMPLE 12

Stabilization of ABS

A solution of 0.25 g of the instant compound of Example 1 in 40 ml of hexane/methanol is added to a rapidly stirred suspension of 100 g of ABS (acrylonitrile/butadiene/styrene terpolymer) in 600 g of water. The suspension is filtered and dried under vacuum at 40° C. for 40 hours. To the dried powder is added 2% by weight of titanium dioxide and 1% by weight of N,N'-ethylenebisstearamide on a two roll mill at 180° C. over four minutes. Compression molded plaques (0.8 ram) are prepared at 175° C. and placed in an air oven at 180° C. for 45 minutes. The color of said plaques are determined as yellowness index values using ASTM D 1925-70. The plaques containing the instant compound of Example 1 exhibit lower yellowness index values (less discoloration) than do the control plaques from unstabilized ABS resin.

What is claimed is:

1. The compound 1,1',1"-nitrilo{triethyl-tris-[2,2'-methylene-bis(4,6-di-tert-butylphenyl)]phosphite} having the formula I

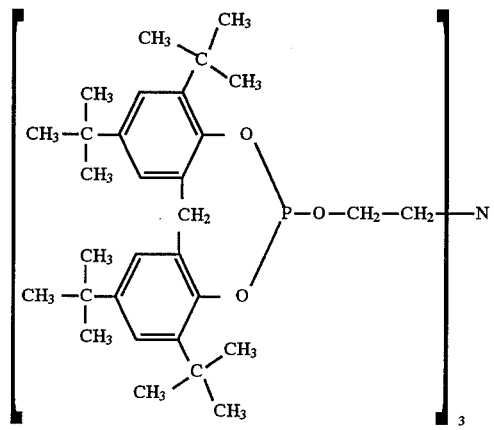

characterized by a glass transition temperature ($T_g$) within the range of 120°–124° C. (DSC) and by an X-ray diffraction pattern which is featureless.

2. A process for the preparation of the amorphous form of the compound 1,1',1"-nitrilo{triethyl-tris-[2,2'-methylene-bis(4,6-di-tert-butylphenyl)]phosphite} having the formula I

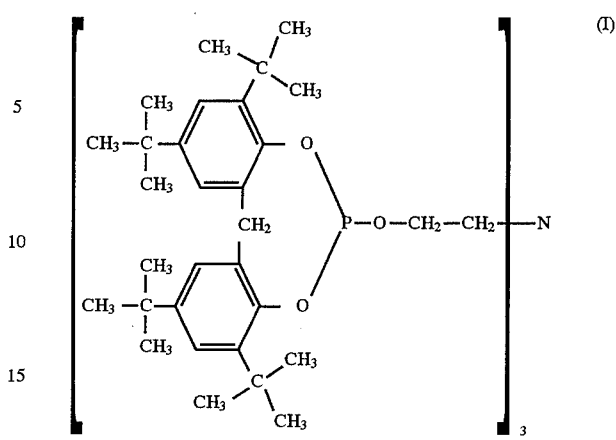

characterized by a glass transition temperature ($T_g$) within the range of 120°–124° C. (DSC) and by an X-ray diffraction pattern which is featureless, which comprises melting said compound and rapidly cooling the melt.

3. A process according to claim 2 which comprises pouring the molten material onto a cool surface maintained below 100° C.

4. A process according to claim 3 wherein the cool surface is near 25° C.

5. A composition stabilized against thermal, oxidative and actinic induced degradation which comprises (a) an organic material subject to thermal, oxidative and actinic induced degradation, and (b) an effective stabilizing mount of the amorphous form of 1,1',1"-nitrilo{triethyl-tris-[2,2'-methylene-bis(4,6-di-tert-butylphenyl)]phosphite} having the formula I

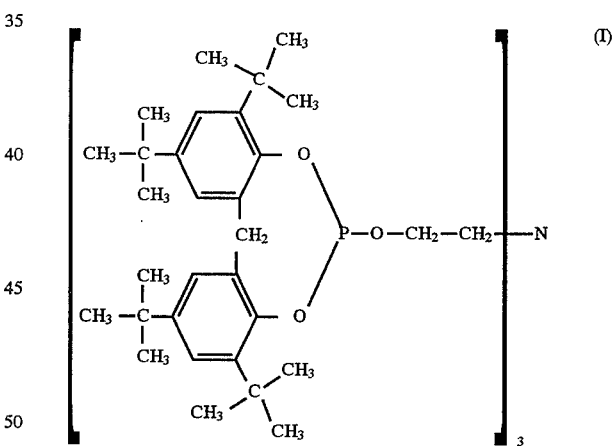

characterized by a glass transition temperature ($T_g$) within the range of 120°–124° C. (DSC) and by an X-ray diffraction pattern which is featureless.

6. A composition according to claim 5 wherein the organic material is a natural, semi-synthetic or synthetic polymer.

7. A composition according to claim 6 wherein the polymer is a thermoplastic polymer.

8. A composition according to claim 7 wherein the polymer is a polyolefin.

9. A composition according to claim 8 wherein the polyolefin is polyethylene or polypropylene.

10. A composition according to claim 9 wherein the polyolefin is polypropylene.

11. A composition according to claim 5 which additionally contains a phenolic antioxidant, a light stabilizer or a processing stabilizer.

12. A composition according to claim 5 which additionally contains as a coadditive at least one compound of the benzofuran-2-one type.

13. A process for stabilizing an organic material against oxidative, thermal or actinic-induced degradation, which comprises incorporating therein or applying thereto the amorphous form of 1,1',1"-nitrilo{triethyl-tris-[2,2'-methylene-bis (4,6-di-tert-butylphenyl)]phosphite} having the formula I according to claim 1.

14. A composition according to claim 5 wherein component (a) is a lubricant, lubricating oil, natural fat or wax, or fat or wax based on a synthetic ester.

* * * * *